United States Patent [19]

Uemura et al.

[11] 4,010,074
[45] Mar. 1, 1977

[54] METHOD FOR PURIFICATION AND RECOVERY OF UROKINASE

[75] Inventors: Yahiro Uemura, Ikeda; Katuhiro Uriyu, Sakai; Satoshi Funakoshi, Katano, all of Japan

[73] Assignee: The Green Cross Corporation, Osaka, Japan

[22] Filed: May 4, 1976

[21] Appl. No.: 683,239

Related U.S. Application Data

[63] Continuation of Ser. No. 537,331, Dec. 30, 1974, abandoned.

[30] Foreign Application Priority Data

Jan. 22, 1974 Japan .............................. 49-10022
Jan. 28, 1974 Japan .............................. 49-12016

[52] U.S. Cl. ............................................ 195/66 B
[51] Int. Cl.² ........................................ C07G 7/02
[58] Field of Search ...................... 195/66 B, 66 R

[56] References Cited

UNITED STATES PATENTS 3,723,251  3/1973  Ogawa et al. .................... 195/66 B
3,746,622  7/1973  Nishikawa et al. .............. 195/66 R

OTHER PUBLICATIONS

Shiba et al., Toho Igakkai Zasshi (Journal Medical Society Toho, Japan), 1973, 20(3.4)280–284; Abstracted in Chemical Abstracts vol. 80, 56897s.

*Primary Examiner*—Lionel M. Shapiro
*Attorney, Agent, or Firm*—Cushman, Darby & Cushman

[57] ABSTRACT

Highly purified urokinase is obtained in a high yield by adsorbing urokinase from an aqueous crude urokuinase solution including human urine at a pH of about 4.0 to about 7.0 on a water-insoluble polysaccharide containing agarose and agaropectin, for example, agar and Sepharose, and by eluting urokinase with an alkaline solution (pH of about 8 to 11) or concentrated salt solution.

14 Claims, No Drawings

METHOD FOR PURIFICATION AND RECOVERY OF UROKINASE

This is a continuation of application Ser. No. 537,331, filed Dec. 30, 1974, now abandoned.

This invention relates to a method for the purification of urokinase. More particularly, this invention is concerned with a simple procedure to yield highly purified urokinase with a high recovery from aqueous crude urokinase solution including human urine.

Urokinase present in human urine catalyzes the conversion of plasminogen to plasmin, which is capable of lysing fibrin clots. Purified urokinase has extensively been used clinically for the therapy of peripheral arterial and venous thrombosis and myocardinl infarction derived from the formation of fibrin clots in blood vessels.

For the purification of urokinase from human urine, various adsorbents such as heavy metals, barium sulfate, silicic acid and its salts and ion exchangers have heretofore been used. (refer to, for example, U.S. Pat. Nos. 3,542,646 and 2,983,647). Accordingly, the conventional methods in which combined application of those adsorbents is employed, have not only been tedious but also led to poor recovery.

The present inventors found that water-insoluble polysaccharide containing agarose and agaropectin as main ingredient are excellent selective adsorbents for urokinase. Based on this finding, the inventors have accomplished the present invention.

An object of the present invention is to provide a method for recovering highly purified urokinase by a simple procedure with good yield.

The above object can be accomplished according to the present invention by a method which comprises selectively adsorbing urokinase from a crude urokinase solution at a pH of from weakly acidic to neutral range on a water-insoluble polysaccharide containing agarose and agaropectin as main ingredient, and then eluting the adsorbed urokinase with an aqueous weak alkaline or concentrated salt solution.

Either human urine as it is or its partially purified preparation according to the present method or the above-mentioned conventional method is used as a source of urokinase in the present invention.

Water-insoluble polyaccharides containing agarose and agaropectin as the main ingredients contain at least 50% of agarose portion. In practice, there are advantageously used inexpensive agar, and commercially available Sepharoses (manufactured by Pharmacia Co. Ltd., Uppsala, Sweden), which are composed mainly of agarose and have been used as molecular sieves hitherto.

Agar is composed of about 70% of agarose and about 30% of agaropectin and quite stable and inexpensive, as is well known. Since agar brings about favorable results in the purification of urokinase, the use thereof in the present invention is recommendable. Powder agar is used as it is, while spongy agar is also used in the form of fine pieces in order to enhance its adsorbing ability.

Sepharoses are classified into Sepharoses 2B, 4B and 6B, depending on the reticular structure of agarose portion therein, and any of these may be used in the present invention. Heretofore, Sepharoses have been used as so-called gel-filtration for separating substances from the mixture having different molecular weight from each other according to the size of molecular weight and the shape. It is noticeable that the present invention has been accomplished by finding the specific adsorbing effects of Sepharoses which effects are entirely different from the above-mentioned molecular sieving effects.

The present inventors have found that agar and Sepharoses selectively adsorb urokinase at a pH of from weakly acidic to neutral. That is, at a pH of about 4.0 to 7.0, preferably 5.0 to 6.0, urokinase is selectively adsorbed on the above-mentioned water-insoluble polysaccharides.

According to the present invention, an aqueous urokinase solution including human urine is adjusted to the above-mentioned pH preferably with buffering salts, and then brought into contact with agar, Sepharose or the like water-insoluble polysaccharide containing agarose and agaropectin as main ingredients which has previously been equilibrated at the same pH preferably with a buffer solution having a pH same as above. The contact may be carried out by passing the urokinase solution through a column of polysaccharide, or by merely stirring a mixture of the polysaccharide and the urokinase solution. The concentration of salt used may be such a low as about 0.03 to 0.15M. The adoption of urokinase at such low concentration facilitates the subsequent elution step with denser salt solution.

The urokinase adsorbed polysaccharide is then contacted with an aqueous alkaline solution or a dense solution of an aqueous neutral salt or neutral amino acid, whereby the urokinase can be selectively eluted. The aqueous alkaline solution used in this case has a pH of about 8.0 to 11.0, preferably 8.0 to 10.5, and is desirably about 2 to 4% aqueous ammonia solution, or an aqueous alkali solution containing about 0.01 to 0.15M of an inorganic salt such as ammonium sulfate, sodium phosphate or sodium chloride, or about 0.5 to 2% (W/V) of an amino acid such as glycine, alginine or histidine. The dense salt solution used is an aqueous solution containing about 0.2 to 2M of an inorganic salt solution, and includes, for example, about 1M of sodium chloride, about 0.5M of ammonium sulfate or about 5 to 10% (W/V) of a neutral amino acid solution.

The effect of purification and concentration of urokinase according to the present invention is enhanced by washing off the impurities from the urokinase-adsorbed adsorbent. The washing salution may be water of pH below 7, but is ordinarily neutral or weakly acidic solution same as used for the adsorption of urokinase. For example, a 0.05M sodium chloride or sodium phosphate solution at a pH of 5.5 to 6.5 can be used. It has been found that the selective removal of impurities can be further enhanced by the addition of certain amino acids or salts thereof into the washing solution. That is, it is effective to use the aforesaid inorganic salt solution at a pH of 5.5 to 6.5 which has been dissolved with 0.05 to 0.1M of lysine, epsilon-aminocaproic acid, glycine, serine, cysteine, histidine or alginine. Among these amino acids, lysine is particularly preferable since it displays the effect even at a low concentration. In the present invention, the adsorption, elution and washing may be conducted with ordinary procedures, and it is most preferable to adopt such procedure that the aqueous solution to be treated is contracted with an adsorbent packed in a column, though this is not limitative.

The urokinase solution, which has been eluted by the method of the present invention, is dialyzed, if necessary, against water or an isotonic solution, and subjected to concentration and sterile filtration in a proper order to obtain a physiologically acceptable urokinase preparation. This preparation can be stored under freeze-dried. This may be formed into a solution at the time of use.

In the present invention, the purity of urokinase is calculated by measuring the enzymatic activity of eluted urokinase solution according to Ploug's method (Ploug: Biochem. Biophys. Acta, Vol. 24, Page 278, 1957), which gives Ploug units per mg protein (the said unit will be referred to as "specific activity" hereinafter). The ratio of the specific activity of the purified urokinase and the starting material indicates the degree of purification attained. The yield can also be calcutated by the same manner as above on the basis of total units.

According to the method of the present invention, urokinase having a specific activity of 7,000 to 10,000 unit/mg. is obtained from human urine by one step-purification procedure, and highly purified urokinase having a specific activity of 20,000 to 30,000 unit/mg. applicable for injection is obtained from partially purified urokinase (300–500 unit/mg.) with a purification degree of more than 30 times, depending on the purity of the starting urokinase solution.

As the method of the present invention is successively applied to human urine, purified urokinase preparation applicable for injection can be simply obtained.

The water-insoluble polysaccharide containing agarose and agaropectin as the main ingredient, which has been used in the present method, can be repeatedly used without loss in adsorption ability by washing with a dilute and slightly alkaline or neutral solution, such as 0.05M sodium chloride solution at a pH of 7.2.

The term "% W/V" referred to herein and in the claims is the weight by part of the solute in 100 parts by volume of the solution.

The present invention is illustrated in detail below with reference to examples. In the examples, the unit of urokinase was measured according to Ploug's fibrin plate method (Ploug: Biochem. Biophys. Acta, Vol. 24, page 278, 1957).

EXAMPLE 1

A suspension of 10 g. of powdery agar (produced by Nakarai Kagaku Co.) in 1,000 ml. of cold water was allowed to stand for 30 minutes, and then the supernatant was discarded by decantation. The precipitate was packed in a column (3 × 15 cm). The column was passed through with 200 ml. of a 0.15M phosphate buffered solution (pH of 5.0). Subsequently, 50 ml. of a partial purified urokinase from fresh human urine (550 unit/mg., 250 unit/ml.) in the same phosphate buffed solution of above, was applied to the column, whereby the urokinase was adsorbed on the column and other impurities were passed through without adsorption. The column was washed out with about 100 ml. of water to remove impurities. Subsequently, urokinase was eluted with 100 ml. of a 1M sodium chloride solution. Fractions containing the urokinase were collected, and dialyzed overnight against an isotonic sodium chloride solution.

Urokinase thus obtained had a specific activity of 17,000 unit/mg. and had been purified 31 times. The recovery thereof was 82%.

EXAMPLE 2

A suspension of 5 g. of agar powder (produced by Difco Co.) in 250 ml. of hot water was formed into a solution by moderately heating for 20 minutes. Insoluble substances were removed by filtration using a No. 2 filter paper (produced by Toyo Filter Paper Co.), and the filtrate was allowed to cool in another vessel and then completely frozen at −30° C. The frozen agar was gradually melted in warm water to obtain porous spongy form, which was then cut into about 0.1 to 1 cm$^3$ pieces.

The pH of urine collected from a human was adjusted to 9.0, and insolubles appeared were removed by centrifugation. Thereafter, the above-mentioned spongy agar was placed into 1,000 ml. of the clarified urine. The pH of the mixture was adjusted to 6.0 with a proper amount of hydrochloric acid and then gently stirred at room temperature for about one hour, whereby urokinase in the urine was adsorbed onto the spongy agar. During this time, the spongy agar was occasionally compressed to promote the adsorption of urokinase. The adsorbed spongy agar was collected by filtration using a gauze, washed with about 500 ml. of a 0.05M sodium chloride solution (pH 5.0) containing 0.1M of lysine followed by about 1,000 ml. of cold distilled water. Subsequently, the adsorbed urokinase was eluted with 200 ml. of a 0.5M ammonium sulfate solution, and the eluates were collected and then dialyzed against a 0.1M phosphate buffer solution (pH 7.0) to obtain 200 ml. of a dialyzed urokinase solution. The specific activity of urokinase thus obtained was 9,000 unit/mg.

EXAMPLE 3

The spongy agar used in Example 2 was packed in a column (3 × 15 cm), washed with about 1,000 ml. of a 0.05M sodium chloride solution (pH 7.2), followed by about 100 ml. of a 0.03M phosphate buffer solution (pH 6.0). The 55 mg. of crude urokinase (specific activity 370 unit/mg) extracted from human urine in 20 ml. of cold water, was applied to the colunn to adsorb the urokinase on the agar. After the column was washed with about 500 ml. of a 0.1M phosphate buffered solution containing 0.05M of epsilon-aminocaproic acid (pH 6.0), followed by 500 ml. of a 0.1M phosphate buffer, to remove the impurities from the column throughly. Then urokinase was eluted from the column with a 0.1M sodium phosphate solution (pH 9.0), and the fractions containing urokinase activity were collected. Urokinase thus obtained had a specific activity of 24,000 unit/mg. and had been purified 65 times, and the recovery thereof was 82%.

EXAMPLE 4

A suspension of 100 ml. of Sepharose 4B (produced by Pharmacia Co., Sweden) in cold water was allowed to stand for one hour, and the supernatant was removed by decantation together with fine Sepharose 4B which was still suspended. The precipitate was packed in a column (3 × 15 cm), and then equilibrated with a 0.1M phosphate buffer (pH 6.0). Subsequently, 3 liters of fresh urine collected from adult males after adjusted the pH to 6.0 with 0.5N-HCl was applied to the column, whereby urokinase was selectively adsorbed on the column, and a major proportion of impurities were passed through the column without absorption. The impurities remaining in the column could be removed substantially by washing the column with 200 ml. of 0.05M sodium chloride solution containing 0.05M lysine-hydrochloride. Subsequently, urokinase was eluted with 100 ml. of 2% ammonia (pH 10.5). The resulting urokinase fractions were freeze-dried to obtain 0.5 mg. of urokinase of a specific activity, 9,400 unit/mg.

EXAMPLE 5

The 700 milliliters of Sepharose 6B (produced by Pharmacia Co., Sweden) were washed with 2,000 ml. of cold distilled water. Separately, 30 liters of fresh urine collected from adult males were diluted with 10 liters of cold water (near neutral). This diluted urine was mixed with the above-mentioned Sepharose 6B, and stirred at room temperature for 30 minutes, whereby urokinase of the mixture was adsorbed on the Sepharose 6B. Subsequently, the Sepharose 6B which had adsorbed the urokinase, was collected by filtration on a filter paper. This adsorbed Sepharose 6B was washed with about 1,000 ml. of cold distilled water, followed by about 1,000 ml. of a 0.1M sodium chloride solution (pH 6) containing 0.1M of glycine. This was added to 500 ml. of a 0.01M sodium phosphate solution (pH 10). After the mixture was allowed to stand at room temperature for 20 to 30 minutes, urokinase dissociated from Sepharose 6B into the solution was separated by vacuum filtration. The pH of this solution was adjusted to 7.2 with hydrochloric acid, and then freeze-dried to obtain about 5 mg. of urokinase of a specific activity of 8,700 unit/mg.

EXAMPLE 6

The whole amount of the Sepharose 6B used in Example 5 was packed in a column, regenerated by washing with a 0.05M sodium chloride solution, and then equilibrated with a 0.1M phosphate buffered solution pH 6. About 4 g. of crude urokinase (specific activity of 430 unit/mg.) in 1,000 ml. of a solution (pH 6) applied on the column, whereby the urokinase was specifically adsorbed on the Sepharose 6B, and a major portion of impurities were passed through the column without being adsorbed. The column was washed with 500 ml. of a 0.05M sodium phosphate solution (pH 6) followed by 1,400 ml. of a 0.05M sodium chloride solution containing 0.05M of lysine hydrochloride (pH 6), whereby the impurities were removed substantially completely.

Urokinase was eluted with about 1,500 ml. of a 0.01M sodium chloride solution adjusted the pH to 9.5 with 1N-sodium hydroxide. Urokinase thus obtained had a specific activity of 32,000 unit/mg and had been purified about 74 times from the starting crude urokinase. The recovery thereof was 96%.

EXAMPLE 7

Example 2 was repeated, provided that the preparation scale of urokinase was enlarged using 30 l. of urine, and 1000 ml. of a dialyzed solution containing urokinase having a specific acitivity of 7,800 unit/mg was obtained.

The solution was further treated according to the procedures described in Example 6. About 1,500 ml. of the solution thus obtained containing urokinase was dialyzed against isotonic sodium chloride solution, and the solution was freeze-dried. 3.5 mg. of urokinase of a specific activity of 37,000 unit/mg was obtained.

What is claimed is:

1. A method for the purification and concentration of urokinase which comprises selectively adsorbing urokinase from an impurity-containing aqueous urokinase solution at a pH ranging from about 4.0 to about 6.0 on a water-insoluble polysaccharide selected from the group consisting of agar and agarose, and thereafter eluting the adsorbed urokinase with an aqueous alkaline solution or a concentrated aqueous salt solution.

2. A method according to claim 1, wherein the impurity-containing aqueous urokinase solution is human urine.

3. A method according to claim 1, wherein the adsorption is effected at a pH of 5.0 to 6.0.

4. A method according to claim 1, wherein the agar is powdery or spongy.

5. A method according to claim 3, wherein the pH is adjusted by means of a buffered salt solution.

6. A method according to claim 5, wherein the buffered salt solution has a salt concentration of about 0.03 to 0.15M.

7. A method according to claim 1, wherein the aqueous alkaline solution has a pH of 8.0 to 11.0.

8. A method according to claim 1, wherein the aqueous alkaline eluting solution contains at a concentration of about 0.01 to 0.15M of an inorganic salt selected from the group consisting of ammonium sulfate, sodium phosphate and sodium chloride.

9. A method according to claim 1, wherein the aqueous alkaline solution contains, at a concentration of about 0.5 to 2% (W/V), an amino acid selected from the group consisting of glycine, arginine and histidine.

10. A method according to claim 1, wherein the aqueous alkaline solution is about 2 to 4% (W/V) aqueous ammonia.

11. A method according to claim 1, wherein the concentrated aqueous salt solution is a 1M aqueous sodium chloride solution or a 0.5M aqueous ammonium sulfate.

12. A method according to claim 1, wherein the water-insoluble polysaccharide is further washed to remove remaining urokinase therefrom with a washing solution selected from the group consisting of water, aqueous sodium chloride and sodium phosphate solutions at a pH of 5.5 to 6.5 and molar concentration of 0.03 to 0.15M.

13. A method according to claim 12, wherein the washing solution additionally contains at a concentration of 0.05 to 0.1M an amino acid selected from the group consisting of lysine, epsilon-aminocaproic acid, glycine, serine and cysteine.

14. A method according to claim 1 wherein the agarose is a Sepharose.

* * * * *